(12) United States Patent
Mehdizadeh

(10) Patent No.: US 6,231,609 B1
(45) Date of Patent: *May 15, 2001

(54) DISC REPLACEMENT PROSTHESIS

(76) Inventor: Hamid M. Mehdizadeh, 14928 Diduca Way, Los Gatos, CA (US) 95032

( * ) Notice: Subject to any disclaimer, the term of this patent is extended or adjusted under 35 U.S.C. 154(b) by 0 days.

This patent is subject to a terminal disclaimer.

(21) Appl. No.: 09/247,696

(22) Filed: Feb. 10, 1999

Related U.S. Application Data

(63) Continuation-in-part of application No. 09/112,865, filed on Jul. 9, 1998, now Pat. No. 5,928,284.

(51) Int. Cl.⁷ ........................................................ A61F 2/44
(52) U.S. Cl. ...................................... 623/17.11; 623/17.13
(58) Field of Search .............................. 623/17.11–17.19, 623/16.11

(56) References Cited

U.S. PATENT DOCUMENTS

| | | | |
|---|---|---|---|
| 5,002,576 | 3/1991 | Fuhrmann et al. | 623/17 |
| 5,401,269 * | 3/1995 | Buttner-Janz et al. | 623/17 |
| 5,458,642 * | 10/1995 | Beer et al. | 623/17 |
| 5,571,190 * | 11/1996 | Ulrich et al. | 623/17 |
| 5,669,909 | 9/1997 | Zdeblick et al. | 606/61 |
| 5,674,296 | 10/1997 | Bryan et al. | 623/17 |
| 5,702,450 * | 12/1997 | Bisserie | 623/17 |
| 5,782,832 * | 7/1998 | Larsen et al. | 606/61 |
| 5,893,889 * | 4/1999 | Harrington | 623/17 |
| 5,928,284 * | 7/1999 | Mehdizadeh | 623/17 |
| 6,019,792 * | 2/2000 | Cauthen | 623/17 |

OTHER PUBLICATIONS

Gill Publication (et al) 1996.
Part I Removal of Disc (Post 1970).
Aronson et al Publication 1982.

* cited by examiner

*Primary Examiner*—Dinh X. Nguyen
*Assistant Examiner*—Alvin Stewart
(74) *Attorney, Agent, or Firm*—Henry M Stanley

(57) ABSTRACT

A disc replacement prosthesis is described which is placed within the intradiscal space vacated by a removed deteriorated disc, and which affords mobility rather than fusion between adjacent vertebral bodies. The prosthesis also protects remaining discs from deterioration by providing a shock absorbing prosthesis portion. Structure is provided that affords resistance to shear force applied to the shock absorbing portion. The prosthesis adheres initially mechanically to the vertebral bodies and adheres through arthrodesis over a period of time.

18 Claims, 3 Drawing Sheets

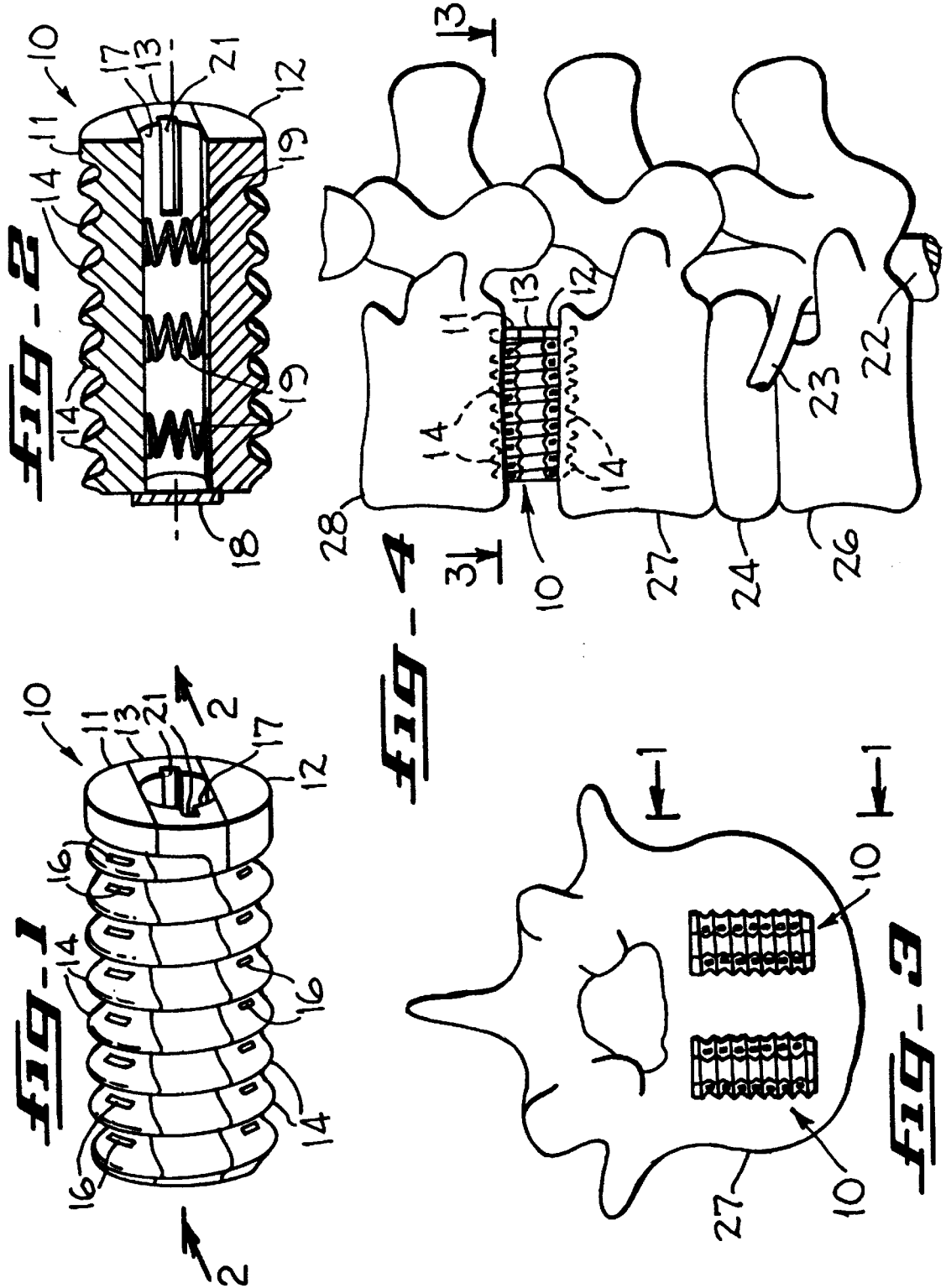

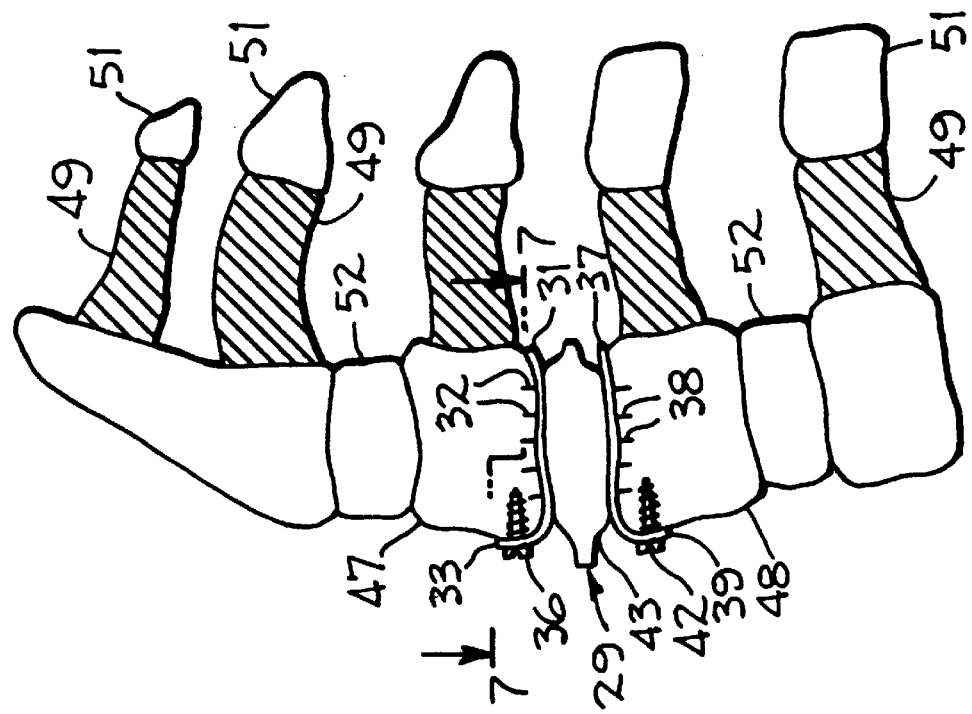
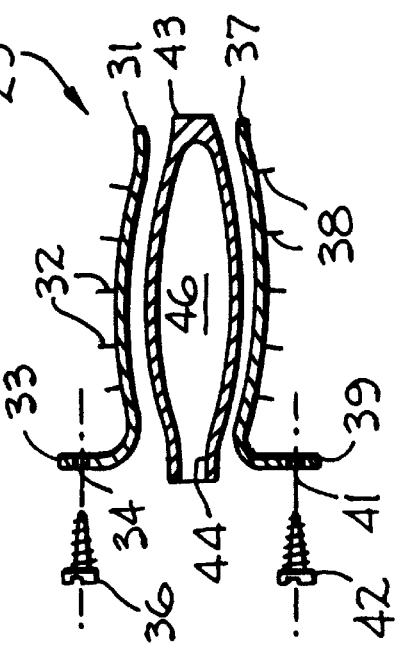
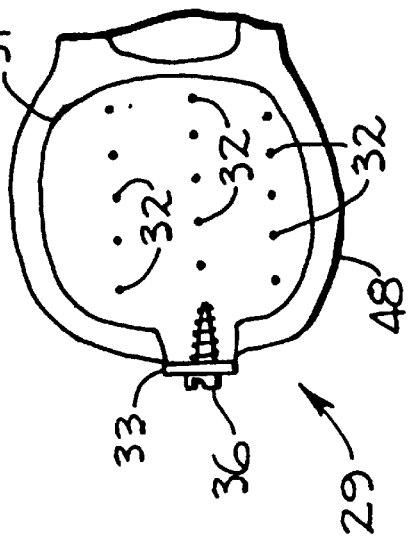

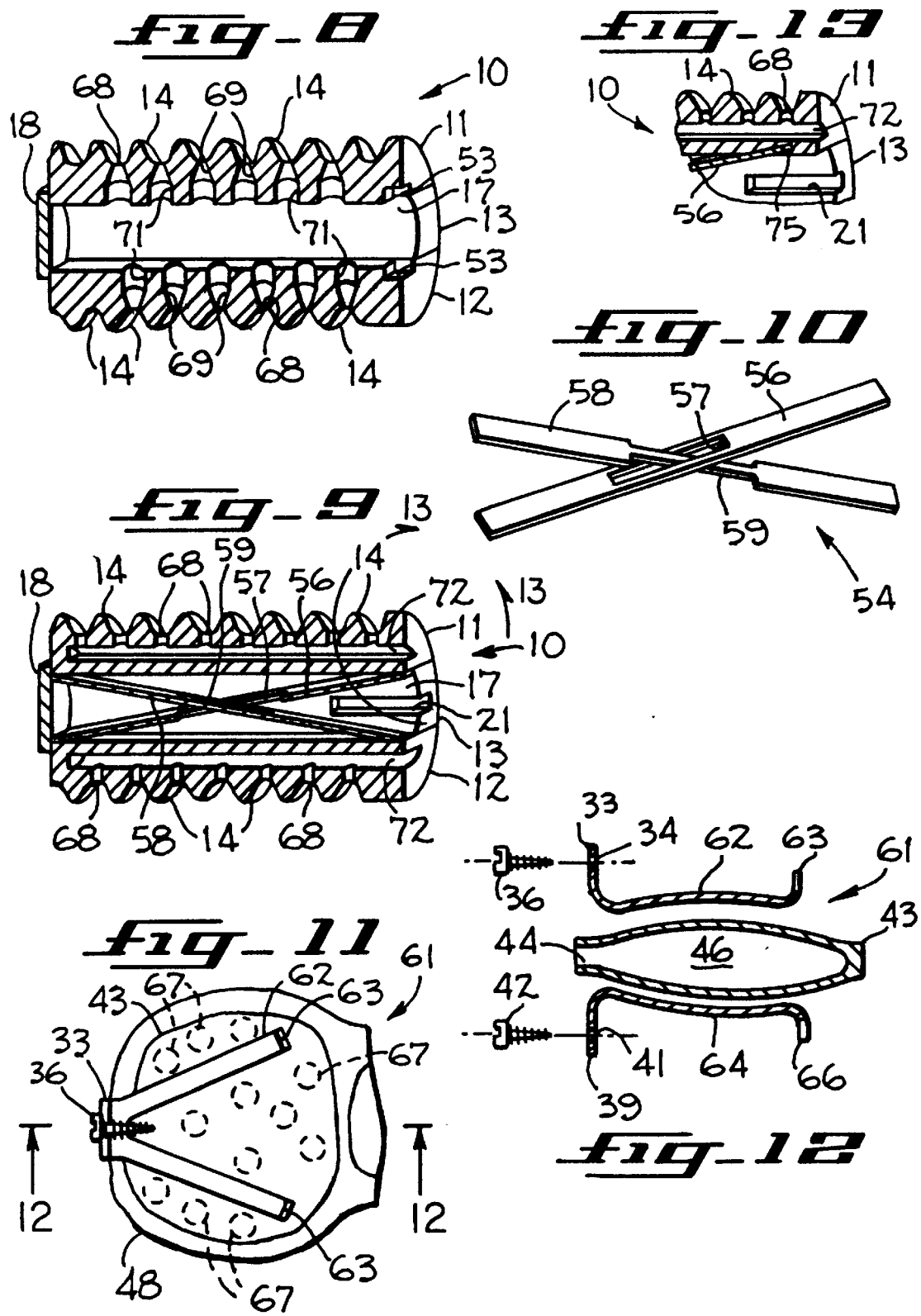

DISC REPLACEMENT PROSTHESIS

This is a Continuation-in-Part patent application of Ser. No. 09/112,865 filed Jul. 9, 1998, now U.S. Pat. No. 5,928,284.

SUMMARY OF THE INVENTION

A disc replacement prosthesis is described for positioning between adjacent superior and inferior vertebral bodies in the spine. Included is an upper cylindrical section for contacting and gripping the superior vertebral body lower surface and a lower cylindrical section for contacting and gripping the inferior vertebral body upper surface. A resilient intermediate cylindrical section is affixed to and extends between the upper and lower means for contacting and gripping. The upper, intermediate and lower sections form a cylinder having an exterior surface when joined, and screw threads are formed on the exterior surface of the cylinder. Structure is provided that affords shear strength in the intermediate cylindrical section.

The invention described herein includes a method of providing a prosthetic replacement for a vertebral disc removed from an intradiscal space between adjacent superior and inferior vertebral bodies wherein the inferior and superior vertebral bodies have lower and upper surfaces respectively adjacent the intradiscal space. The method includes the steps of fabricating an upper and a lower rigid member having surfaces thereon which are porous to living bone cells, and configuring the upper and lower rigid members for retention by the adjacent superior and inferior vertebral bodies respectively. Further included are the steps of attaching a resilient member between the upper and lower rigid members to produce a disc prosthesis and engaging the lower and upper surfaces on the vertebral bodies with the upper and lower rigid members respectively as well as strengthening the resilient member to resist shear forces.

In accordance with the invention described herein a prosthesis is disclosed for replacing a disc removed from an intradiscal space between adjacent superior and inferior vertebral bodies. An upper prosthesis member is included having a contact surface configured to engage and become fixed to a lower surface on the superior vertebral body. Furthermore, a lower prosthesis member is included having a contact surface configured to engage and become fixed to an upper surface on the inferior vertebral body. An intermediate elastomeric prosthesis member is fixed to and extends between the upper and lower prosthesis members. Means is included for securing the upper and lower prosthesis members in place and in contact with the superior and inferior vertebral bodies, respectively. Structure is provided for imparting shear strength to the intermediate elastomeric prosthesis member. The upper and lower prosthesis member contact surfaces have a porosity for admitting bone cell growth for enhancing arthrodesis.

A disc replacement prosthesis has upper means for contacting and gripping a lower surface on a superior vertebral body and lower means for contacting and gripping an upper surface on an inferior vertebral body. Resilient intermediate means is affixed to and extends between the upper and lower means. Additionally, means is provided for affording resistance to shear force applied to the resilient intermediate means.

The invention further includes a method of making a disc replacement prosthesis having an upper and a lower body compatible rigid member and an intermediate body compatible resilient member. The method involves the steps of treating the upper and lower rigid members to enhance bone cell growth into the surfaces thereof and fixing the upper and lower rigid members onto opposing sides of the intermediate resilient member. Also included is the step of providing shear force resistance for the intermediate resilient member.

BRIEF DESCRIPTION OF THE DRAWINGS

FIG. 1 is a perspective of one embodiment of the present invention.

FIG. 2 is a section along the line 2—2 of FIG. 1.

FIG. 3 is a section along the line 3—3 of FIG. 4.

FIG. 4 shows the embodiment of FIG. 1 disposed between adjacent vertebral bodies.

FIG. 5 is an exploded section of an additional embodiment of the present invention.

FIG. 6 shows the embodiment of FIG. 5 disposed between adjacent vertebral bodies.

FIG. 7 is a section along the line 7—7 of FIG. 6.

FIG. 8 is a section along the line 2—2 of FIG. 1 showing another embodiment of the invention.

FIG. 9 is a section along the line 2—2 of FIG. 1 showing an additional embodiment of the invention.

FIG. 10 is a perspective of a crossed flat spring arrangement used in the present invention.

FIG. 11 is a plan view of another embodiment of the invention shown in FIG. 7.

FIG. 12 is an exploded section along the line 12—12 of FIG. 11.

FIG. 13 is a detail taken from the portion 13—13 of FIG. 9.

DESCRIPTION OF THE PREFERRED EMBODIMENTS

The history of surgical procedures for correction of spinal deformity goes back many years and, when the procedures relate to problems caused by intravertebral disc deterioration, always includes fusion of two or more vertebrae through the use of rods, clamps, wires, bone plugs, and various intradiscal space fusion devices. The purpose in these procedures has always been to immobilize two or more vertebrae to remove or reduce pain emanating from pressure on the cauda equina or nerve roots extending therefrom. By way of example, a nerve root retractor and disc space spreader is described and claimed in the applicant's U.S. Pat. No. 5,803,904 issued Sep. 8, 1998 which is useful in a surgical procedure for implanting a threaded fusion cage in the intradiscal space vacated by a removed disc. The nerve root retractor of the aforementioned patent is also useful, together with the other instruments described therein, for placing the embodiment of the present invention as seen in FIG. 1 between adjacent vertebral bodies within the vacated intradiscal space. Previous to the advent of the present invention when a vertebral disc was removed and adjacent vertebral bodies fused, deterioration of the remaining discs in the spinal column occurred because the cumulative shock absorption capability of the spine was reduced by removal of one of the spine's shock absorbing components, the disc. In all cases of vertebral fusion, accelerated deterioration of remaining discs is inevitable. It may be seen from the following description that through the use of the invention disclosed and claimed herein, not only is it possible to relieve pressure on the cauda equina and the nerve roots, but it is also possible to replace a removed disc and retain the shock absorbing characteristics of the replaced disc.

Referring to FIG. 1 of the drawings, a disc replacement prosthesis 10 is shown having an upper rigid member 11 and a lower rigid member 12. An intermediate resilient portion 13 is shown extending between and attached to the upper and lower metallic members 11 and 12. The intermediate portion 13 is fabricated of some body compatible material such as polypropylene or silicone elastomer. The upper and lower metallic members 11 and 12, respectively, are also formed of some body compatible material such as titanium or Hedrocel (TM) in a preferred embodiment. The upper, lower and intermediate members shown in FIG. 1 are fixed together as by a body compatible cement to form a cylindrical prosthesis. The cement is capable of fixing the members together as a unit and is resistant to shear and tensile stress. The outer surface of the prosthesis 10 has screw threads 14 formed thereon and also has holes 16 extending through rigid members 11 and 12 which communicate with an axial channel 17 extending along the length of the prosthesis 10. The channel 17 may extend along the entire axial length of the prosthesis 10, or it may be capped at one end as shown by the cap 18 (FIG. 2), or it may only extend part way along the axial length of the prosthesis according to the surgical purposes for which the prosthesis is used. For example, additional vertical stiffness may be imparted to the prosthesis for upward and downward forces exerted against the lower and upper rigid portions 12 and 11, respectively, by filling the channel 17 with additional body compatible elastomeric substance and retaining it within the channel 17 by use of the cap 18 fixed at one or both ends of the channel. Alternatively, as seen in FIG. 2, a selectable level of vertical stiffness is obtainable with a series of coil springs 19 affixed between the upper and lower rigid members 11 and 12 as by welding opposing ends of the springs 19 to the rigid members. The springs 19 provide an assisting resistance to shear forces applied to the intermediate resilient portion 13 of the embodiment of FIG. 2. Additionally, variable vertical stiffness from prosthesis to prosthesis is obtainable when the body compatible elastomeric substance is used in conjunction with the coil springs 19.

With reference to FIG. 10 a crossed spring assembly shown generally at 54, includes a first flat spring 56 having a centrally located aperture 57 therein. A second flat spring 58 is also included having a reduced width section 59 in the center portion thereof. First flat spring 56 is fixed as by welding at an upper end to the under side of upper member 11 and at a lower end to the upper side of lower member 12 as seen in FIG. 9. The first and second flat springs are assembled within channel 17 by passing the smaller dimension of spring 58 through aperture 57 until reduced width section 59 is within aperture 57 and then rotating spring 58 about its long axis to assume the attitude seen in FIG. 10. The upper end of second flat spring 58 is then fixed, as previously mentioned, to the under side of upper member 11 and the lower end thereof is fixed to the upper side of lower member 12, whereupon the spring assembly 54 in the configuration of FIG. 10 is fixed within the channel 17 as depicted in FIG. 9.

When the flat spring assembly 54 is used and when it is desirable to minimize the increase in spring stiffness in a vertical direction of the assembly as viewed in FIG. 9, the ends of the flat springs 56 and 58 are not fixed to the inside surfaces of upper and lower members 11 and 12 as by welding. In such a case, referring now to FIG. 13, a slot 75 is cut at an angle to the inside surfaces of the upper and lower members as shown in FIG. 13. One such slot 75 is cut in two places, angled in opposing directions, on the inside surfaces of upper rigid member 11 and lower rigid member 12 at positions thereon corresponding substantially to the positions where flat springs 56 and 58 contact each of the rigid members. The slots are angled to align with the flat spring lengths as they approach the inside surfaces of the rigid members 11 and 12. The slot widths are only wide enough to allow entry of the flat spring ends. As a result, instead of fixing the flat spring ends as by welding, each of the four ends of the two flat springs are placed within one of the angled slots 75 to assume a configuration similar to that of FIG. 9. The flat springs are said to be captured between the upper and lower rigid members in this configuration as opposed to being fixed therebetween. The flat springs are inserted only part way into the depth of the slot 75 to leave a space between the spring end and the slot end as shown in FIG. 13. The assembly may have to be held in a jig at this point to hold the springs in position so their ends are spaced from the slot ends. The aforementioned fill of the center channel 17 with a body compatible elastomer is then performed. After the body compatible elastomer has cured, the assembly 10 with crossed flat springs is complete. When vertical force is exerted against the assembly of FIG. 9, the force is absorbed wholly by the elastomer in channel 17 and the resilient member 13 until the ends of the flat springs 56 and 58 both slide into contact with the ends of slots 75. In any event, shear force applied to intermediate resilient member 13 is resisted as hereinafter described. Alternative means for holding the flat springs within channel 17 without fixing the spring ends are envisioned.

A variety of flat spring assembly configurations, such as configurations utilizing bowed or looped springs oriented as the spring assembly 54, are envisioned to perform the desired function. It may be seen that the members within the spring assembly 54 and its equivalents mentioned herein are flat springs. Flat springs have a lower spring coefficient or stiffness (force per unit of deflection) for force applied against the broad flat side and a higher spring coefficient or stiffness for force applied against an edge. The lower spring coefficient is aligned with forces that tend to compress intermediate resilient member 13 as seen in FIG. 9. This installation will be referred to as installing the spring in parallel with resilient member 13. The higher spring coefficient is aligned with forces that tend to produce shear in member 13. The shear force applied to resilient member 13 to be resisted is defined in the following paragraph. It should be noted that similar relative spring characteristics for compression and shear forces are obtained through the use of coil springs 19 of the type shown in FIG. 2.

The purpose of the crossed spring configuration of the embodiment of FIG. 9 is to provide additional shear strength in the pictured embodiment to resist opposing forces on upper and lower members 11 and 12 applied laterally to the axis of channel 17 which would apply shear forces to intermediate elastomeric portion 13. Those forces would be substantially into and out of the plane of the paper as is shown in FIG. 9. In addition, the assembly of FIG. 9 resists opposing forces on the upper and lower members 11 and 12 within the plane of the paper in directions along the longitudinal axis of the embodiment of FIG. 9 which would also stress intermediate elastomeric portion 13 in shear.

As further seen in FIGS. 1 and 2, a proximal end of the prosthesis 10 has a configuration such as the opposed keyways 21 (one shown only) in the end of intermediate resilient portion 13 for engagement by a cage insertion instrument to accomplish placement within the intradiscal space as is known in the threaded fusion cage surgical process. A pair of opposing keyways 53 in the ends of the upper and lower rigid members 11 and 12 is also envisioned as seen in FIG. 8 to fulfill the same purpose as the keyways 21. A known vertebral drill and vertebral tap are used together with the nerve root retractor and disc space spreader of the aforementioned invention described in U.S. Pat. No. 5,803,904 to prepare the intradiscal space and to place the prosthesis 10 within the intradiscal space as shown in FIG. 4 of the drawings. FIG. 4 also shows a portion of the cauda equina 22 with a nerve root 23 extending therefrom past a healthy disc 24 situated between a vertebral body 26 and a vertebral body 27. The prosthesis 10 is shown situated below and having upper rigid member 11 in contact with a lower threaded surface on a superior vertebral body 28. In like fashion, the threaded portion of lower rigid member 12 is in contact with an upper threaded surface on the inferior vertebral body 27 in FIG. 4. The aforementioned lower and upper surfaces of the adjacent vertebral bodies 28 and 27, respectively, have been tapped by the aforementioned vertebral tap to place threads therein which match the threads 14 on the prosthesis 10. The prosthesis is seen to be placed in FIG. 4 so that vertical force exerted thereupon will be absorbed by the resilient member 13 and any elastomeric filling substance within channel 17 and/or by the coil springs 19 or cross spring assembly 54 contained within channel 17.

FIG. 8 shows the prosthesis 10 having openings 68 in the grooves of the threads 14 on upper and lower rigid members 11 and 12. Conical voids 69 are in communication with the openings 68. Cylindrical voids 71 are formed in the inside surfaces of the upper and lower members 11 and 12 which communicate with and provide access for formation of the conical voids 69. When the prosthesis 10 is in place, as described herein, the openings 68 allow bone cell growth therethrough into the conical voids 69 which, in time, fixes each prosthesis 10 within the intradiscal space. The channel 17 is empty as depicted in FIG. 8 for clarity. The channel includes any combination of body compatible material, coil springs 19, or cross spring assembly 54 as a surgeon and circumstances dictate. When the channel 17 is filled only with a body compatible elastomer, such as a silicone, without including coil springs 19 or a flat spring configuration such as crossed spring assembly 54, the configuration of upper and lower rigid members 11 and 12 seen in FIG. 8 is used. The cylindrical voids 71, accepting some elastomer, assist in retaining the elastomer within channel 17 during use. The aforementioned bone growth through openings 68 extending into the conical voids 69 still occurs to fix the prothesis in place.

In FIG. 9 the openings 68 are once again seen in the grooves of the threads 14. The openings extend through the body of the upper and lower rigid members 11 and 12 and communicate with an elongated channel 72 within the body of members 11 and 12. As in the embodiment of FIG. 8, when the prosthesis 10 is in an intradiscal space the openings 68 allow bone cell growth therethrough into the elongated channel 72. The bone cell growth functions to fix the prosthesis in place, ultimately performing the function initially performed by the screw threads 14.

With reference to FIG. 3, it may be seen that the prosthesis 10 is used in pairs to provide stability in the spinal column. As a result, mobility is retained between the vertebral bodies 27 and 28 rather than fusion and remaining discs, such as disc 24, are protected from deterioration because the pair of prostheses 10 (FIG. 3) retain most of the shock absorbing characteristics of the natural disc which they replace. While the prosthesis 10 is seen to be useful for replacement of discs in the lumbar region of the spine, it is envisioned that it may be used in other portions, such as the cervical portions, of the spine as well.

Referring now to FIG. 5 of the drawings, an exploded elevation of an alternative embodiment of the prosthesis of the present invention is shown at 29. An upper member or metallic plate 31 is shown having an upper surface from which a number of upwardly extending pins 32 about 2 mm. long project. Upper metallic member 31 also has a tab 33 with a hole 34 therethrough for receiving a screw 36. A lower metallic member or plate 37 is shown having a number of short pins 38 about 2 mm. long extending downward therefrom. In like fashion, the lower metallic plate 37 has a downwardly extending tab 39 having a hole 41 therethrough for receiving a screw 42. The upper and lower metallic plates 31 and 37 are fabricated from titanium or Hedrocel (TM) material as mentioned hereinbefore for the metallic cylindrical sections 11 and 12 in the embodiment of FIG. 1. The plates 31 and 37 when fabricated from titanium material are hydroxy apatite or bone morphogenic protein (BMP) treated to provide a surface which is porous to growing bone cells. Hedrocel (TM) material is also useful for fabricating the plates 31 and 37 as it also provides a surface that is porous to living bone cells.

Continuing with the description of the embodiment of FIG. 5 showing the prosthesis 29, a bag of some material that is body compatible such as polypropylene is shown at 43. The bag has an opening 44 at one end through which an elastomeric substance may be deposited within a chamber 46 within the bag.

With reference to FIG. 6, the prosthesis 29 is shown in place between the lower surface of a superior vertebra 47 and the upper surface of an inferior vertebra 48. FIG. 6 shows a cervical portion of the spine wherein shaded areas 49 represent bone and cartilage extending from the anterior portions of the vertebral bodies 47 and 48 toward posterior portions 51. The anterior portions of the vertebral bodies are of interest in this disclosure since nondeteriorated discs 52 are shown in place between vertebral bodies in FIG. 6.

Upper plate 31 is shown in FIG. 6 attached by the screw 36 through the tab 33 to the superior vertebral body 47. The pins 32 are shown penetrating the lower surface of the superior vertebral body 47 to assist in fixing the metallic plate 31 in place initially before the bone cells are afforded an opportunity to grow into the porous surface of the plate.

In FIG. 6 the lower metallic plate 37 is shown fixed to the upper surface of the inferior vertebral body 48 by means of the screw 42 through the tab 39 and the pins 38 projecting downwardly from the metal plate 37 into the structure of the inferior vertebral body 48. The screws 36 and 42 are shown being introduced into the anterior portion of the vertebral bodies 47 and 48 because operations in the cervical portion of the spine are generally through an anterior opening. In like fashion, the opening 44 in the bag 43 is shown in the anterior portion of the bag so that the elastomeric material may be injected into the chamber 46 within the bag and the opening 44 sealed from the front. The upper surface of the bag 43 is fixed by a body compatible adhesive to the lower surface of the upper plate 31 and the lower surface of the bag 43 is fixed by such an adhesive to the upper surface of the lower plate 37. Once the cushion afforded by the bag 43 is appropriately filled and sized vertically and the opening 44 is sealed, the edges of the bag 43 are trimmed to cause the cushion to lie within the confines previously occupied by the removed deteriorated disc.

FIG. 12 shows an alternative embodiment of that shown in FIG. 5. An exploded elevation of a prosthesis 61 is depicted wherein components having structure and function similar to the structure and function of components in FIG.

5 are assigned the same item numbers. An upper "V" shaped member 62 has two arms joined at the upturned tab 33 (FIG. 11) with the hole 34 therethrough formed to accept passage of the screw 36. The free ends of the arms on the "V" shaped member 62 have upturned sharp points or spikes 63 thereon. In like fashion a lower "V" shaped member 64 has two arms thereon joined at the downwardly extending tab 39 (FIG. 12) with the hole 41 therethrough for accepting the screw 42. The free ends of the arms on the "V" shaped member 64 have downwardly extending points or spikes 66 thereon. The "V" shaped members 62 and 64 are preferably made using either hydroxy apatite or BMP treated titanium or Hedrocel (TM) material, both of which provide surfaces porous to living bone cells.

The bag 43, made of a body compatible material, as mentioned hereinbefore, has the aforementioned opening 44 therein through which an elastomeric substance is deposited in the chamber 46. The upper and lower surfaces of the bag 43 which are exposed to the lower surface of superior vertebral body 47 and upper surface of inferior vertebral body 48 respectively, are treated in the exposed portions with dots of hydroxy appetite or BMP as seen at 67 in FIG. 11. Alternatively, the entire exposed surface of the bag 43 is so treated as long as bone cell growth into the surface of the bag is encouraged and bag flexibility is maintained.

The placement of the disc prosthesis 61 of FIGS. 11 and 12 is shown in FIG. 6, wherein the upwardly and downwardly extending points 63 and 66 on the upper and lower "V" shaped members 62 and 64 take the place of the pins 32 and 38 and are caused to penetrate the adjacent lower and upper surfaces of vertebral bodies 47 and 48 to assist in fixing the "V" shaped members in place temporarily until bone cell growth fixes them in place as described herein. Upper "V" shaped member 62 is secured to the anterior portion of superior vertebral body 47 with screw 36 through hole 34 and lower "V" shaped member 64 is secured to the anterior portion of lower vertebral body 48 with screw 42 through hole 41 in the fashion seen in FIG. 6. The upper surface of the bag 43 is fixed to the underside of "V" shaped member 62 by a body compatible cement. In similar fashion, the lower surface of bag 43 is fixed to the upper side of "V" shaped member 64. The bag 43 is filled through opening 44 with a flowing silicon or some other bio-compatible material and opening 44 is then sealed. The fill within compartment 46 is, in some circumstances, expandable to insure a snug fit within the intradiscal space, thereby enhancing spinal stability.

As stated hereinbefore for the embodiment of the prosthesis shown in FIGS. 1 and 2, the prostheses 29 and 61 shown in FIGS. 5–7, 11 and 12 protect healthy discs 52 by affording the shock absorbing capabilities of the replaced disc and also affording mobility between the superior vertebral body 47 and the inferior vertebral body 48 rather than fusion therebetween. The prostheses as finally installed are seen in FIGS. 7 and 11 to occupy that space normally taken up by the replaced disc. Following temporary retention in place by the pins 32 or the points 63 and 66 and the screws 36 and 42, the prostheses 29 and 61 are held securely by bone cell growth within the surface of the plates 31 and 32 (FIG. 7) or the surfaces of bag 43 and the "V" shaped members 62 and 64, whether they be hydroxy apatite treated or BMP treated or Hedrocel (TM) material.

As recited hereinbefore, the method of providing a prosthetic replacement for a vertebral disc removed from an intradiscal space between adjacent superior and inferior vertebrae includes treating an upper and a lower rigid member to produce a surface thereon which is porous to living bone cells. Subsequent attachment of a resilient member between the upper and lower metallic members produces a disc prosthesis. The disc prosthesis is placed in the intradiscal space in contact with the adjacent vertebral bodies and is then secured in place, at least temporarily, by mechanical means. The resilient portion of the prosthesis is filled with a body compatible elastomeric substance. The mechanical securing of the metallic portions of the prosthesis may be obtained by the screw threads of the prosthesis 10 of FIGS. 1 and 2 or by the pins 32 and 38 or points 63 and 66 and the screws 36 and 42 of the prostheses 29 and 61 of FIGS. 5–7 or 11 and 12, respectively. While the prostheses 10, 29 and 61 have been described individually as useful in the lumbar or cervical regions of the spine, their use is envisioned as possible in any region of the spine when appropriately sized and when circumstances permit.

Although the best modes contemplated for carrying out the present invention have been shown and described herein, it will be understood that modification and variation may be made without departing from what is regarded to be the subject matter of the invention.

What is claimed is:

1. A disc replacement prosthesis for positioning between adjacent superior and inferior vertebral bodies, comprising upper means for contacting and gripping a lower surface on the superior vertebral body, lower means for contacting and gripping an upper surface on the inferior vertebral body, resilient intermediate means affixed to and extending between said upper and lower means for contacting and gripping, and a dual stiffness spring extending between said upper and lower means for contacting and gripping, said dual stiffness spring having a first stiffness aligned to absorb forces placing said resilient intermediate means in shear, and a second low stiffness aligned to absorb forces placing said resilient intermediate means in compression.

2. The disc replacement prosthesis of claim 1 wherein said dual stiffness spring comprises flat spring means fixed to and between said upper and lower means for contacting and gripping.

3. The disc replacement prosthesis of claim 1 wherein said dual stiffness spring comprises spring means captured between and extending between said upper and lower means for contacting and gripping, and means for retaining said spring means in captured position.

4. The disc replacement prosthesis of claim 3 wherein said dual stiffness spring comprises a flat spring.

5. The disc replacement prosthesis of claim 1 wherein said upper means comprises an upper cylindrical section, wherein said lower means comprises a lower cylindrical section, and wherein said resilient intermediate means comprises an intermediate cylindrical section, said lower, upper and intermediate sections forming a cylinder having an exterior surface when joined together, further comprising screw threads on said exterior surface.

6. The disc replacement prosthesis of claim 5 wherein said cylinder has an anterior end and a posterior end, comprising means at said anterior end for engagement by a prosthesis insertion instrument.

7. The disc replacement prosthesis of claim 5 wherein said cylinder has a channel extending axially therealong, comprising body compatible elastomeric substance within said channel.

8. The disc replacement prosthesis of claim 1 wherein said upper and lower means for contacting have outer surfaces, having apertures therein in communication with at least one internal chamber therewithin, whereby bone cell growth from adjacent bone structure through said apertures into said at least one internal chamber fixes the disc replacement prosthesis in place.

9. The disc replacement prosthesis of claim 1 wherein said upper and lower means for contacting comprise metallic members, said metallic members having surface treatment for enhancing bone cell growth.

10. A method of making a disc replacement prosthesis having an upper and a lower body compatible rigid member and an intermediate body compatible resilient member subject to shear force in one direction and subject to compressive force in a direction orthogonal to said one direction, comprising the steps of treating the upper and lower rigid members to enhance bone cell growth into the surfaces thereof, positioning and fixing the upper and lower rigid members on opposing sides of the intermediate resilient member, providing a dual stiffness spring having a high spring stiffness for resisting force applied thereto in one direction and a low spring stiffness for resisting force applied thereto orthogonally to said one direction, and mounting said dual stiffness spring between said upper and lower body compatible rigid members with said high spring stiffness aligned to resist shear force in said intermediate body compatible resilient member and with said low spring stiffness aligned to resist compressive force in said intermediate body compatible resilient member.

11. The method of claim 10 wherein the upper and lower rigid members fixed on opposing sides of the intermediate resilient member form a compartment therebetween, comprising the step of filling the compartment with a body compatible resilient substance.

12. The method of claim 10 wherein the step of mounting said dual stiffness spring comprises the step of capturing the spring between the upper and lower body compatible rigid members in parallel with the intermediate resilient member.

13. A disc replacement prosthesis for positioning between adjacent superior and inferior vertebral bodies in the spine comprising upper means for contacting and gripping the superior vertebral body lower surface, lower means for contacting and gripping the inferior vertebral body upper surface, resilient intermediate means affixed to and extending between said upper and lower means for contacting and gripping, wherein said upper means comprises an upper cylindrical section, said lower means comprises a lower cylindrical section, and said resilient intermediate means comprises an intermediate cylindrical section, said upper cylindrical section, lower cylindrical section and intermediate cylindrical section forming a cylinder having an exterior surface when joined together, further comprising a spring assembly extending between said upper means and said lower means, said string assembly having a dual spring stiffness, wherein a first lower spring stiffness is aligned to absorb force applied to said upper means and said lower means that compresses said resilient intermediate means and wherein a second higher spring stiffness is aligned to absorb force applied to said upper means and said lower means that induces shear stress in said resilient intermediate means.

14. The disc replacement prosthesis of claim 13 wherein said spring assembly comprises, crossed flat spring means.

15. The disc replacement prosthesis of claim 13 wherein said upper and lower cylindrical sections have opposing keyways therein configured to receive a prosthesis insertion instrument.

16. A method of providing a prosthetic replacement for a vertebral disc removed from an intradiscal space between adjacent superior and inferior vertebral bodies, wherein the superior and inferior vertebral bodies have lower and upper surfaces respectively adjacent the intradiscal space, comprising the steps of fabricating an upper and a lower rigid member having surfaces thereon which are porous to living bone cells, configuring the upper and lower rigid members for at least temporary retention by the adjacent lower and upper surfaces on the superior and inferior vertebral bodies respectively, attaching a resilient member to and between the upper and lower rigid members to produce a disc prosthesis, engaging the lower and upper surfaces on the vertebral bodies with the upper and lower rigid members respectively, providing a dual stiffness spring having a high spring stiffness for resisting force applied in one direction and a low spring stiffness for resisting force applied orthogonally to said one direction, aligning said high spring stiffness to resist force placing said resilient member in shear, and aligning said low spring stiffness to resist force placing said resilient member in compression.

17. A prosthesis for replacing a disc removed from an intradiscal space between adjacent superior and inferior vertebral bodies, comprising an upper prosthesis member having a contact surface configured to engage and become fixed to a lower surface on the superior vertebral body, a lower prosthesis member having a contact surface configured to engage and become fixed to an upper surface on the inferior vertebral body, an intermediate elastomeric prosthesis member fixed to and extending between said upper and lower prosthesis members, a crossed flat spring assembly extending between said upper and lower prosthesis members aligned to absorb compression within and to impart shear strength to said intermediate elastomeric prosthesis member, and means for securing said upper and lower prosthesis members in place in contact with the superior and inferior vertebral bodies respectively, said upper and lower prosthesis member contact surfaces having a porosity for admitting bone cell growth for enhancing arthrodesis.

18. The prosthesis of claim 17 wherein said upper prosthesis member comprises an upper cylindrical section, said lower prosthesis member comprises a lower cylindrical section and said intermediate elastomeric member comprises an intermediate cylindrical section, so that the prosthesis is a cylinder having a cylindrical surface, said means for securing comprising screw threads on said cylindrical surface.

* * * * *